(12) United States Patent
Ebert et al.

(10) Patent No.: US 10,274,408 B2
(45) Date of Patent: Apr. 30, 2019

(54) CROSS-SENSITIVITY-COMPENSATED BIOSENSOR

(71) Applicant: Biotronik SE & Co. KG, Berlin (DE)

(72) Inventors: Henning Ebert, Berlin (DE); Andreas Bunge, Leipzig (DE)

(73) Assignee: Biotronik SE & Co. KG, Berlin (DE)

( * ) Notice: Subject to any disclaimer, the term of this patent is extended or adjusted under 35 U.S.C. 154(b) by 227 days.

(21) Appl. No.: 15/169,369

(22) Filed: May 31, 2016

(65) Prior Publication Data

US 2016/0349162 A1 Dec. 1, 2016

(30) Foreign Application Priority Data

Jun. 1, 2015 (DE) .................. 10 2015 108 644

(51) Int. Cl.
*G01N 7/04* (2006.01)
*A61B 5/00* (2006.01)
(Continued)

(52) U.S. Cl.
CPC ............ *G01N 7/04* (2013.01); *A61B 5/1495* (2013.01); *A61B 5/14532* (2013.01); *A61B 5/14546* (2013.01); *A61B 5/14735* (2013.01); *A61B 5/6867* (2013.01); *G01N 7/10* (2013.01); *G01N 15/06* (2013.01); *G01N 33/49* (2013.01); *A61B 2560/0247* (2013.01);
(Continued)

(58) Field of Classification Search
CPC combination set(s) only.
See application file for complete search history.

(56) References Cited

U.S. PATENT DOCUMENTS 5,005,403 A 4/1991 Steudle et al.
5,337,747 A 8/1994 Neftel
(Continued)

FOREIGN PATENT DOCUMENTS

DE 69017428 T2 9/1995
DE 10311622 A1 10/2004
(Continued)

OTHER PUBLICATIONS

German Search Report received in DE102015108644.1, dated Aug. 17, 2015, 5 pages.
(Continued)

*Primary Examiner* — Brian R Gordon
(74) *Attorney, Agent, or Firm* — Arc IP Law, PC; Joseph J. Mayo (57) ABSTRACT

Embodiments of the invention include a biosensor, such as an implantable biosensor, that includes a sensor material sensitive to at least one analyte in a pressure measurement chamber coupled to a pressure sensor. In embodiments of the invention, a pressure prevailing in the pressure measurement chamber may be determined by the pressure sensor. The sensor material is coupled in the pressure measurement chamber to a compensation material, which includes a relationship between a temperature and a volume of the pressure. The relationship is opposite to a temperature-dependent change in pressure or volume of the sensor material and at least partially compensates for a cross-sensitivity-induced change in volume of the sensor material.

16 Claims, 3 Drawing Sheets

(51) Int. Cl.
*A61B 5/145* (2006.01)
*A61B 5/1473* (2006.01)
*A61B 5/1495* (2006.01)
*G01N 7/10* (2006.01)
*G01N 33/49* (2006.01)
*G01N 15/06* (2006.01)
*G01N 15/00* (2006.01)

(52) U.S. Cl.
CPC . *A61B 2562/0247* (2013.01); *A61B 2562/168* (2013.01); *G01N 2015/0065* (2013.01)

(56) References Cited

U.S. PATENT DOCUMENTS

| | | | |
|---|---|---|---|
| 6,117,086 A * | 9/2000 | Shulze | A61B 5/0215 600/486 |
| 6,268,161 B1 * | 7/2001 | Han | A61B 5/0031 435/14 |
| 6,475,750 B1 | 11/2002 | Han et al. | |
| 6,546,268 B1 | 4/2003 | Ishikawa et al. | |
| 7,553,280 B2 | 6/2009 | Lesho | |
| 2001/0016683 A1 | 8/2001 | Darrow et al. | |
| 2002/0155425 A1 | 10/2002 | Han et al. | |
| 2005/0154272 A1 | 7/2005 | Dirac et al. | |
| 2009/0013791 A1 * | 1/2009 | Zdeblick | A61B 5/0215 73/700 |
| 2009/0241681 A1 | 10/2009 | Machauf et al. | |
| 2009/0275815 A1 | 11/2009 | Bickoff et al. | |
| 2010/0056888 A1 | 3/2010 | Skerl et al. | |
| 2011/0124985 A1 | 5/2011 | Meurville et al. | |
| 2016/0150959 A1 * | 6/2016 | Mizrahi | A61B 5/6843 600/430 |
| 2016/0287101 A1 * | 10/2016 | Tai | A61B 5/02141 |
| 2016/0365198 A1 * | 12/2016 | Pan | G01L 1/02 |
| 2018/0103872 A1 * | 4/2018 | Forsell | A61B 17/12009 |

FOREIGN PATENT DOCUMENTS

| | | |
|---|---|---|
| DE | 10311623 A1 | 10/2004 |
| WO | 2003061475 A1 | 7/2003 |
| WO | 2008102001 A1 | 8/2008 |

OTHER PUBLICATIONS

European Search Report received in 16172071.9, dated Nov. 14, 2016, 5 pages.

* cited by examiner

CROSS-SENSITIVITY-COMPENSATED BIOSENSOR

This application claims the benefit of German Patent Application No. DE 10 2015108644.1, filed on 1 Jun. 2015, the specification of which is hereby incorporated herein by reference.

BACKGROUND OF THE INVENTION

Field of the Invention

Embodiments of the invention generally relate to a cross-sensitivity-compensated biosensor.

Description of the Related Art

Hereinafter, a sensor used for the detection or concentration determination of analytes in media inside or outside a human or animal body will be referred to as a biosensor. In addition, hereinafter, a medium that potentially contains an analyte which is to be detected or of which the concentration is to be determined will be referred to as a test medium.

Generally, in order to provide new sensors for the concentration determination or the detection of substances, polymer networks may be used. Polymer networks are polymers of which the molecules are chemically linked (for example by covalent or ionic bonds) or physically linked (for example by entanglement of the polymer chains) to form a three-dimensional network. A network of this type swells in the presence of an opportune solvent by absorbing the solvent. Typically, the swollen network is then also referred to as a gel or polymer gel. If water is the swelling agent, reference is also made to a hydrogel. As special gels, "smart" gels ("smart" hydrogels when water is used as swelling agent) have the ability under certain preconditions to selectively respond to changes in ambient variables, this response being manifested by changes in volume. Sensitivities may be attained in particular with respect to temperature, pH value, ion concentration, or substance concentration. Such polymer networks may thus respond by means of a significant volume change as a result of water uptake or water release in the event of a change to the concentration of a substance, for example in the blood. Introduced into a defined volume, the concentration-dependent volume change may be converted into a concentration-dependent pressure change. This is relevant in particular in the case of sensors by means of which the concentration of certain substances (for example what are known as biomarkers, for example in the blood) may be determined.

For the production of "smart" gels, base materials are often used that, besides being dependent on the sensitivities to the substances for detection or concentration determination of which said materials have been produced, additionally are heavily dependent on other ion or substance concentrations and/or temperature and/or pH value, i.e. these gels may change their solvent content (or volume) depending on ion or substance concentrations and/or depending on temperature and/or pH value. The volume change or pressure change of the gel are thus dependent on the concentration of the substance, i.e. the actual sensor measurand, and the concentration of other ion and/or substance concentrations and/or the temperature and/or pH value. It has been found that the volume change or swelling pressure change in the event of variations in temperature and/or pH value are much greater than those volume or swelling pressure changes caused by a change to the actual sensor measurand, for example the concentration of the blood component when using "smart" hydrogels.

The sensitivity of a sensor to variables other than the variable to be measured is referred to as cross-sensitivity. The variable to be measured is the measurand or also sensor measurand. A variable that is not the measurand, however, influences the information delivered by the measuring device concerning the measured value, i.e. is an influencing variable. The influencing variable means that the measured value changes merely as a result of a change to the influencing variable.

United States Patent Publication 2010/0056888 A1, to Skerl et al., entitled "Implantable Biosensor and Sensor Arrangement", discloses an implantable biosensor, in which a hydrogel may be used for the detection of an analyte. As disclosed in Skerl et al., a hydrogel may undergo a significant volume change in the presence of a suitable analyte. According to Skerl et al., pressure sensors are used in order to measure a concentration of an analyte. One measures the pressure in a measurement chamber, which pressure may vary by the analyte, whereas another measures the pressure outside the measurement chamber. In Skerl et al., the content of the analyte in the measurement chamber is determined from the pressure difference. The two pressure values may also be used for temperature compensation.

For example, United States Patent Publication 2009/0275815 A1, to Bickoff et al., entitled "Temperature-Compensated In-Vivo Sensor", discloses a system comprising a biosensor for measuring the concentration of an analyte and a temperature sensor, which detects the temperature in a region as close to the biosensor as possible. In Bickoff et al., the output signal of the biosensor is corrected with the measured temperature in order to determine the measured analyte concentration.

The high technical demands on the sensor system, such as measurement ranges and resolution of the pressure and temperature sensor, may be satisfied only with difficulty for the highly precise detection of medically relevant concentration changes in the blood, in particular in a transportable or implantable system.

BRIEF SUMMARY OF THE INVENTION

One or more embodiments of the invention include an improved cross-sensitivity-compensated biosensor, which allows a reliable and precise detection of analytes to occur.

At least one embodiment of the invention is achieved in accordance with elements of the independent claim. Embodiments of the invention will emerge from the further claims, the description and the drawings as presented herein.

One or more embodiments of the invention include a biosensor that includes a sensor material that is sensitive to at least one analyte. In at least one embodiment, the sensor material is in a pressure measurement chamber coupled to a pressure sensor. In one or more embodiments, a pressure prevailing in the pressure measurement chamber may be determined by the pressure sensor. In at least one embodiment, the sensor material may be coupled in the pressure measurement chamber to a compensation material, which compensates at least in part for a cross-sensitivity-induced change in volume of the sensor material.

By way of one or more embodiments, a pressure sensor may include any device that may determine the pressure prevailing in the pressure measurement chamber.

In at least one embodiment, the biosensor may include a biosensor implantable in a human or animal body.

In one or more embodiments, the sensor material sensitive to at least one analyte is preferably a polymer gel, or hydrogel, or "smart" hydrogel sensitive to at least one analyte.

In one or more embodiments, the sensor is introduced, for the measurement, into a test medium in which the at least one analyte may be contained and of which the presence and/or concentration is determined. In at least one embodiment, an analyte-dependent sensor signal, for example a concentration-dependent sensor signal, may be completely or at least predominantly independent of cross-sensitivity due to the coupled use of the sensor material and compensation material in the pressure measurement chamber. At the same time, in one or more embodiments, the sensitivity to the at least one analyte, for example a blood component, and therefore the concentration-dependent pressure change remains unchanged.

According to at least one embodiment, to compensate for the cross-sensitivity dependency of the sensor signal, the compensation material in the biosensor may mechanically decouple the cross-sensitivity effect of the sensor material from the concentration-dependent sensor signal, such that the concentration-dependent sensor signal is independent of the cross-sensitivity.

In one or more embodiments, the cross-sensitivity-induced change in volume to the sensor material may be one or more of a temperature-dependent volume change and a pH value-induced volume change.

Embodiments of the invention solve a central problem of biosensors including the detection or concentration determination of substances, wherein the biosensors may be based on a swelling pressure measurement of hydrogels that are one or more of temperature-sensitive and sensitive to pH value. In at least one embodiment, one or more of the temperature dependency and the pH value dependency may be mechanically decoupled from the sensitivity to the at least one analyte or analytes, such that a concentration-dependent swelling pressure includes a reduced, or even no longer includes any temperature dependency and/or pH value dependency.

For compensation of the temperature dependency and/or pH value dependency of the sensor signal, in one or more embodiments, the compensation material in the biosensor may mechanically decouple the temperature effect and/or pH value effect of the sensor material, such as of the hydrogel, from the concentration-dependent sensor signal. As such, in at least one embodiment, the concentration-dependent sensor signal may be independent of temperature and/or independent of pH value.

In one or more embodiments, the compensation or at least reduction of the temperature-induced and/or pH value-induced pressure change of the hydrogel may be implemented by a mechanical design. As such, at least one embodiment of the invention may include pressure sensors that have a much smaller measurement range and greater measurement resolution. In one or more embodiments, the measurement resolution to determine the sensor measurand may be increased and for example may enable the determination of physiologically relevant concentration fluctuations in the implant model.

One or more embodiments may include biosensors based on "smart" hydrogels that determine the concentration of substances or that detect substances. In at least one embodiment, smart hydrogels include a special type of hydrogels. In one or more embodiments, in isobaric conditions, such as during free swelling at atmospheric pressure, the smart hydrogels may respond to very minor changes in certain ambient variables, including temperature, pH value, ion or substance concentrations, using volume changes. In at least one embodiment, such hydrogels may include polymer networks, which respond to a stimulus, such as a change in the concentration of a substance in the tested medium, for example blood, using a significant volume change as a result of water absorption and water release. Introduced into a defined volume, in one or more embodiments, the concentration-dependent volume change may be converted into a concentration-dependent pressure change. In at least one embodiment with implantable biosensors, the concentrations of certain substances, for example what are known as biomarkers, may be determined in bodily fluids, such as blood. Generally, in prior art systems, the necessary high demands on the pressure and temperature sensors and/or probes contained in the biosensor for determining a pH value clearly, from a technical and economical viewpoint, do not support a realization of sensors based on hydrogels, such as for mobile use as an implant. According to one or more embodiments of the invention, it may not be necessary to keep the temperature and/or the pH value constantly in the measurement range or to use highly precise pressure and temperature sensors and/or probes in order to determine a pH value. In at least one embodiment, the biosensor may be used in an organism that has fluctuating temperatures and/or pH values, for example in the presence of fever or in the presence of other influences.

In one or more embodiments, using the biosensor, a multiplicity of substances may be specifically detected, or the concentration thereof may be determined. In at least one embodiment, the multiplicity of substances may include one or more of electrolytes, carbohydrates, fatty acids, lipids, sugars, nucleotides, deoxyribonucleic acids, ribonucleic acids, amino acids, peptides, proteins, antibodies, hormones, neurotransmitters, metabolites, metabolic products, antigens, active substances, drugs, nanoparticles, toxins and any other appropriate substance as one skilled in the art would appreciate. In one or more embodiments, the sensitivity to the substance to be detected, referred to herein as analyte, may be achieved via components that are introduced into the hydrogel network, for example covalently.

In at least one embodiment of the invention, a volume effect of the sensor material based on a cross-sensitivity of the sensor material and on a change in concentration of the analyte may be determined at the sensor material.

In at least one embodiment of the invention, a volume effect of the sensor material based on a change in one or more of the pH value and a temperature change, and/or based on a change in concentration of the analyte, may be determined at the sensor material.

By way of one or more embodiments, the "smart" hydrogels may include base materials that, besides the sensitivity to the at least one analyte in question, may include a strong temperature dependency and/or pH value dependency, wherein such smart hydrogels may change their water content depending on the temperature.

In at least one embodiment, when the hydrogel swells up or shrinks back freely, this may be identified based on a significant change in volume; wherein when the hydrogel is limited to a given volume, the pressure in the volume changes accordingly. In one or more embodiments, due to the pronounced temperature dependency and/or pH value dependency, the water release and therefore volume or pressure change may be amplified in the event of a change in concentration of the substances at constant measurement temperature and/or at constant pH value.

In at least one embodiment, the volume and pressure change of the hydrogel may be dependent on the concentration of the analyte, which includes the actual sensor measurand, and may be dependent on one or more of the temperature and the pH value. In one or more embodiments, due to the compensation material, the presence and/or the concentration of the analyte may be determined precisely. In at least one embodiment, the volume change or swelling pressure change may be greater in the case of variations in temperature and/or pH value than volume or swelling pressure changes caused by a change to the actual sensor measurand, for example the concentration of the blood component.

In one or more embodiments, a hydrogel may be used to determine the concentration or to detect the substances relevant from a medical, biochemical, molecular biological, biotechnological or environmental viewpoint. In at least one embodiment, biosensor may be used to detect or determine the concentration of physiologically relevant markers, such as electrolytes, carbohydrates and proteins.

According to one or more embodiments, a hydrogel, besides the sensitivity to the substance, may include a temperature dependency and/or a pH value dependency, wherein the hydrogel may release water or may absorb water depending on the concentration of the substance, the temperature, and the pH value. In at least one embodiment, the water release or absorption may be noticed in a concentration-dependent, temperature-dependent and pH value-dependent swelling pressure, which may be determined using the pressure sensor. In one or more embodiments, the pressure changes produced as a result of temperature and concentration changes and changes to the pH value may be determined.

At least one embodiment of the invention may include a hydrogel that includes, for example, a negative relationship between temperature and volume. For example, in one or more embodiments, when the temperature rises, the volume decreases as a result of water release and the measured pressure influenced by temperature change thus decreases. For example, in at least one embodiment, when temperature decreases, the volume increases as a result of water absorption and the measured pressure influenced by temperature change thus rises. In one or more embodiments, in order to partially or fully mechanically compensate for the temperature dependency, the compensation material may be introduced into the biosensor in contact with the hydrogel. In at least one embodiment, the compensation material, in contrast to the hydrogel, includes an opposite relationship, for example a positive relationship between volume and temperature, wherein when temperature rises the volume and therefore the measured pressure influenced by temperature change increases, and wherein when temperature decreases the volume and therefore the measured pressure influenced by temperature change decreases. In one or more embodiments, the absolute value of the change in volume of the compensation material may be identical to the absolute value of the change in volume of the hydrogel. In at least one embodiment, if complete compensation of the temperature effect is not desired, the absolute values may also differ from one another.

By way of one or more embodiments, to provide a negative relationship between temperature and volume, the hydrogels may include a lower critical solution temperature (LCST). In at least one embodiment, the hydrogel is swollen, for example high swelling pressure, below the LCST, and the hydrogel is collapsed, for example low swelling pressure, above the LCST. In embodiments of the invention, one or more of the following hydrogels with LCST may be used to provide the negative relationship: poly(N-isopropylacrylamide), methacrylate macromonomers (ether-ester structure), poly(N,N-diethylacrylamide), poly(N-vinylcaprolactam), poly[2-(dimethylamino)ethyl methacrylate], poly(ethylene glycol) (PEG), PEG methacrylate, diethylene glycol methyl ether methacrylate, oligo(ethylene glycol) methyl ether methacrylate, and poly(methyl vinyl ether).

At least one embodiment of the invention may include hydrogels with an "upper critical solution temperature" (UCST), with volume increase with rising temperature, or may include hydrogels with a mixture of both UCST and LCST hydrogels. One or more embodiments of the invention may include hydrogels that include both a UCST and an LCST.

In addition to or alternatively to the temperature dependency, at least one embodiment may include a hydrogel that includes a negative relationship between pH value and volume. For example, in one or more embodiments, when the pH value increases, the volume decreases by water release and therefore the measured pressure influenced by a change in the pH value decreases, and when the pH value decreases, the value the volume increases as a result of water absorption and therefore the measured pressure influenced by a change in the pH value rises. In order to partially or fully mechanically compensate for the pH value dependency, by way of at least one embodiment, the compensation material may be introduced into the biosensor in contact with the hydrogel, wherein the compensation material may include, in contrast to the hydrogel, an opposite relationship, for example a positive relationship, between volume and pH value. For example, in one or more embodiments, with an increase of the pH value, the volume and therefore the measured pressure influenced by a change in pH value increases, and with a reduction of the pH value, the volume and therefore the measured pressure influenced by a change in the pH value decreases. In at least one embodiment, the absolute value of the change in volume of the compensation material may be identical to the absolute value of the change in volume of the hydrogel. In one or more embodiments, if complete compensation of the pH effect is not desired, the absolute values may also differ from one another.

In order to provide a negative relationship between pH value and volume, at least one embodiment of the invention may include hydrogels with basic groups, wherein such hydrogels include an increased volume at lower pH values, and wherein the volume is smaller at higher pH values.

In order to form a positive relationship between pH value and volume, one or more embodiments of the invention may include hydrogels with acidic groups, wherein such hydrogels include an increased volume at higher pH values, and wherein the volume is smaller at lower pH values.

In order to provide an alternating relationship between pH value and volume, at least one embodiment of the invention may include hydrogels with both basic and acidic groups, wherein such hydrogels include an increased volume at lower pH values, wherein the volume reduces at medium pH values, and wherein the volume is increased at higher pH values.

In one or more embodiments, to compensate for the respective change in volume depending on pH value, the hydrogels may be expediently combined in sensors.

In at least one embodiment of the invention, the pressure measurement chamber may include at least two compartments, wherein the sensor material may be arranged in a first of the two compartments and the compensation material may be arranged in a second of the two compartments. In one or more embodiments, the first of the two compartments may include a region that is permeable for the analyte and the test medium. In at least one embodiment, the compartments may border one another directly or may be distanced from one another. In the latter case, however, in one or more embodiments, the two compartments may be interconnected In at least one embodiment of the invention, a flexible membrane may be arranged between the two compartments. In one or more embodiments, both compartments may include a region that is permeable for the analyte and the test medium. By way of at least one embodiment, when the compensation material comes into contact with the test medium containing the analyte, the compensation material may be used to also compensate for other cross-sensitivities of the sensor material besides the temperature dependency.

In one or more embodiments, the invention may be extended to all polymer-based sensors for compensation of cross-sensitivities. In at least one embodiment, the sensitivity of the sensor material and of the compensation material of the biosensor to certain analytes, for example blood components, may be determined, for example in polymer-based systems such as hydrogel, by the used polymer system.

In at least one embodiment of the invention, the pressure sensor may be arranged at least in part in the second compartment and may be surrounded at least in regions by the compensation material. In one or more embodiments, the compensation material may be or may include oil. In at least one embodiment, the compensation material may be used to transfer pressure between the sensor material in the first compartment and the pressure sensor in the second compartment. In one or more embodiments, the pressure sensor may be expediently surrounded by the oil. In at least one embodiment, the second compartment may not be permeable for the test medium or the analyte.

According to one or more embodiments, oil includes a positive relationship between temperature and volume, wherein a hydrogel includes a negative relationship between temperature and volume. In at least one embodiment, the thermally induced expansion of the used oil with rising temperature and therefore the temperature-induced pressure rise may be compensated for mechanically.

In one or more embodiments, the sensor material may be mixed in the pressure measurement chamber with the compensation material, such that sensor material and compensation material may be arranged in one compartment. In at least one embodiment, the one compartment may include a region that is permeable for the analyte and the test medium. In one or more embodiments, sensor material and compensation material may fully or at least partially compensate for their volume changes depending on material selection. In at least one embodiment, the sensor material together with the compensation material may form a stack arrangement having alternating layers of sensor material and compensation material. In one or more embodiments, the stack may be formed by, or may include, sheets placed on top of one another or may be formed by application of a coating, for example spincoating. In at least one embodiment, a mixture of particles of sensor material and compensation material may be provided.

In at least one embodiment of the invention, the pressure sensor may be arranged within the pressure measurement chamber in an additional compartment. In one or more embodiments, depending on the type of pressure sensor, the additional compartment may be filled with a pressure transfer medium. In at least one embodiment, the arrangement of the pressure sensor within the pressure measurement chamber in an additional compartment may be expedient when the sensor material and the compensation material are present mixed together in one compartment or are arranged in two adjacent compartments and the compensation material is not the pressure transfer medium in which the pressure sensor is arranged.

In at least one embodiment of the invention, the pressure sensor may be arranged outside the pressure measurement chamber in an additional compartment, which is filled with a pressure transfer medium. In one or more embodiments, such an arrangement may be expedient when the sensor material and the compensation material are present mixed together in one compartment or are arranged in two adjacent compartments and the compensation material is not the pressure transfer medium in which the pressure sensor is arranged.

In at least one embodiment of the invention, the pressure sensor may be connected to the wall of the pressure measurement chamber, or one or more components of the pressure sensor may be part of the wall of the pressure measurement chamber. In one or more embodiments, such an arrangement of the pressure sensor may be expedient when mechanical deformations of the pressure measurement chamber are used to measure the pressure.

In at least one embodiment of the invention, the first compartment may be coupled to the second compartment by a pressure piston connection, such that a change in volume of the first compartment leads to a change in volume of the second compartment.

In at least one embodiment of the invention, the first compartment may be coupled to the second compartment by an extendable pipe connection, such that a change in volume of the first compartment leads to a change in volume of the second compartment. In one or more embodiments, such an arrangement allows for a coordination of dimensions of the biosensor and of the pressure measurement chamber.

In at least one embodiment of the invention, the compensation material may be or may include a hydrogel. In one or more embodiments, the hydrogel may include a relationship of temperature and/or pH value and volume opposite to that of the sensor material, wherein the absolute value of the change in volume of the compensation material may be identical to the absolute value of the change in volume of the sensor material. In at least one embodiment, if complete compensation of the temperature effect and/or the pH value effect is not desired, the absolute values may also be different from one another.

In at least one embodiment of the invention, the biosensor may be used to detect or to concentrate measurement of components in the blood, such as to detect of concentrate measurement of glucose or potassium.

One or more embodiments of the invention may perform a specific detection or concentration determination of a multiplicity of substances or may determine the concentration thereof. In at least one embodiment, the multiplicity of substances may include one or more of electrolytes, carbohydrates, fatty acids, lipids, sugars, nucleotides, deoxyribonucleic acids, ribonucleic acids, amino acids, peptides, proteins, antibodies, hormones, neurotransmitters, metabolites, metabolic products, antigens, active substances, drugs, nanoparticles, toxins and any other appropriate substance as one skilled in the art would appreciate. By way of at least one embodiment, the sensitivity to the substance to be detected (analyte) may be achieved via molecule parts that are introduced into the hydrogel network, for example covalently.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

In the figures, functionally like or similarly acting elements are referenced in each case using the same reference signs. The figures are schematic illustrations of the invention, and are not limited to specific parameters of the invention. Furthermore, the figures reproduce one or more embodiments of the invention and are not intended to limit the invention to the illustrated embodiments.

Figure 1:
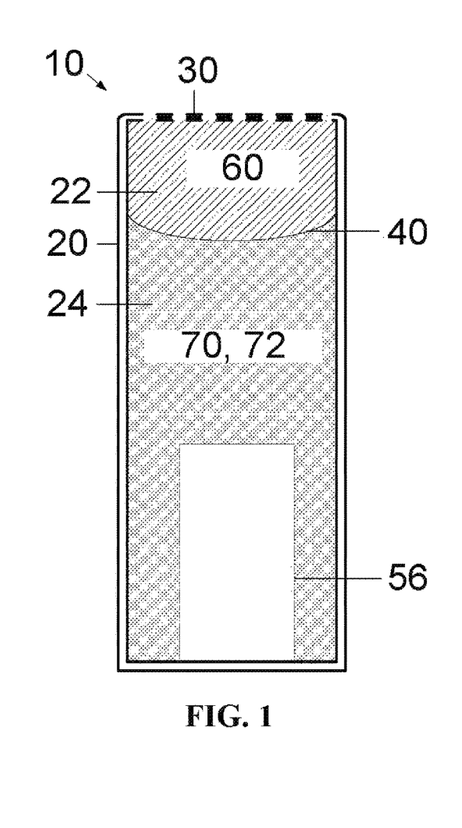
FIG. 1 shows a schematic illustration in section of a first variant of a biosensor according to at least one embodiment of the invention.

FIG. 1, according to one or more embodiments of the invention, shows a first variant of a biosensor 10. In at least one embodiment, the biosensor 10 may be an implantable biosensor and may include a sensor material 60 sensitive to at least one analyte, such as a hydrogel sensitive to at least one analyte. In one or more embodiments, the sensor material 60 may be arranged in a compartment 22 of a pressure measurement chamber 20 and may be coupled to a compensation material 70 in a second compartment 24 of the pressure measurement chamber 20. In at least one embodiment, the compensation material 70 may be, may be formed by, or may include oil 72.

In one or more embodiments, the two compartments 22, 24 may be separated by a flexible membrane 40. In at least one embodiment, the flexible membrane 40 is flexible such that it may forward a change in volume of the sensor material 60 onto the compensation material 70. In one or more embodiments, the compensation material 70 may include a relationship between temperature and volume opposite that of the sensor material 60, such that a change in volume of the sensor material 60 and of the compensation materials 70 caused by a change in temperature is fully compensated for when both materials 60, 70 are fully coordinated with one another.

According to at least one embodiment, the overall volume of the hydrogel, such as sensor material 60, may be approximately constant, for example including isochoric behaviour, on account of its encapsulation in the first compartment 22 of the pressure measurement chamber 20. In one or more embodiments, the pressure rises when the swelling pressure of the hydrogel, such as sensor material 60, increases in the compartment 22. In at least one embodiment, the relationship may be dependent on the cross-sensitivity, for example temperature, and the measurement effect, for example a change in the concentration of the analyte in the test medium.

One or more embodiments of the invention may include a pressure sensor 56, for example an ASIC module, that may be located in the oil 72 in the second compartment 24. In at least one embodiment, the pressure of the surrounding oil 72 may be measured. In one or more embodiments, the measured pressure may be conveyed via the membrane 40 to the oil 72 and the pressure sensor 56 embedded therein. In at least one embodiment, the hydrogel may be coupled as sensor material 60 via the membrane 40. In one or more embodiments, the test medium may be in contact with the hydrogel, such as sensor material 60, via a mechanical abutment 30, which is permeable to the medium and the analyte and may be embodied in the form of a porous membrane.

In at least one embodiment of the invention, the sensor material 60 may include a chemo-mechanical converter, which converts the concentration of the test medium into a physical pressure. In one or more embodiments, the pressure sensor 56 may correspond to a mechano-electrical converter, which remodels the physical pressure into a signal that may be further processed, from which for example an analyte concentration in the test medium may be determined.

At least one embodiment may include "smart" hydrogels as sensor material 60. In one or more embodiments, smart hydrogels include a special type of hydrogels. In isobaric conditions, for example free swelling at atmospheric pressure, in at least one embodiment of the invention, the smart hydrogels respond using volume changes to very minor changes in certain ambient variables, which may include temperature, pH value, ion or substance concentrations. In one or more embodiments, due to the resultant swelling forces, the smart hydrogels may perform mechanical work. In at least one embodiment, in isochoric conditions, for example at constant volume, the change in the ambient variable may lead to a pressure change. In one or more embodiments, the analytes to be detected may penetrate the hydrogel from the outside through the mechanical abutment 30 permeable to the medium and the analyte, wherein the abutment 30 may be embodied in the form of, or may include, a porous membrane. In at least one embodiment, due to the combination of response to ambient variables and change in volume or pressure, hydrogels may include both sensor functionalities and actuator functionalities.

One or more embodiments may include LCST hydrogels as sensor material 60, which include a negative relationship between temperature and volume.

In at least one embodiment, the degree of compensation of the temperature effect of sensor material 60 and compensation material 70 may be determined by coordination of hydrogel volume and oil volume in the two compartments 22, 24.

According to one or more embodiments, LCST hydrogels swell with decreasing temperature, such that the swelling pressure increases, for example as cross-sensitivity. In at least one embodiment, the swelling pressure change caused by the measurement effect, for example by a change in concentration in the test medium, may be much smaller than the temperature effect. In one or more embodiments, the compensation material 70 in the form of oil 72 shrinks with decreasing temperature. In at least one embodiment, the cross-sensitivity may be compensated for by offsetting the temperature-induced swelling of the hydrogel, such as sensor material 60, by the volume reduction of the oil 72.

In one or more embodiments, the sensitivity for the ambient variables may be achieved by use of hydrogel modules, which include special affinities for external stimuli. By way of at least one embodiment, the hydrogel modules, and as a result also the hydrogels, may identify substances in a specific manner, for example in accordance with the key-lock principal, complexing, or other physicochemical interactions.

In one or more embodiments, in order to obtain a complete compensation of the temperature effect in the sensor material 60 and in the compensation material (1:1 conversion), an estimation of the oil volume/hydrogel dry mass ratio may be provided. For example, in at least one embodiment, compensation means that $\Delta V_{oil}/\Delta T = -\Delta V_{HG}/\Delta T$, wherein the temperature-induced change in the oil volume corresponds to the temperature-induced change in the hydrogel volume accompanied by water absorption/release.

In one or more embodiments, for a present hydrogel, such as sensor material 60, a ratio $V_{72}/m_{60}$ of the oil volume $V_{72}$ to the dry mass of the hydrogel $m_{60}$, such as sensor material 60, of $V_{72}/m_{60}=360$ μl/mg is given. In at least one embodiment, in an implantable biosensor 10, a filling with $m_{60}=2$ mg may be provided. In one or more embodiments, for complete compensation, an oil volume $V_{72}$ of 720 μl may be used. In at least one embodiment, the hydrogel, such as sensor material 60, may be adapted with respect to the swelling properties, wherein the temperature dependency of the swelling may be reduced and increased. By way of one or more embodiments, the necessary oil quantity $V_{72}$ may be reduced or increased. In at least one embodiment, hydrogels in which the ratio is considerably different, for example 10,000 μl/mg, 1,000 μl/mg, 100 μl/mg, 10 μl/mg, 1 μl/mg, or 0.1 μl/mg, may be used as sensor material 60. In one or more embodiments, if complete compensation or an overcompensation of the temperature dependency is not desired, the ratio $V_{72}/m_{60}$ of the oil volume $V_{72}$ to the dry mass may be adapted accordingly.

In at least one embodiment, small quantities of the hydrogels, such as sensor material 60, may be introduced into the compartment 22 of the biosensor 10, for example via spin-coating, and for larger quantities of the hydrogels, particles and/or sheets may be used. In one or more embodiments, the hydrogels, such as sensor material 60, may be synthesised directly in the biosensor 10.

In at least one embodiment of the invention, the membrane 40 between the compartment 22 that includes the sensor material 60 and the compartment 24 that includes the compensation material 70, in this case oil 72, may be very flexible.

Figure 2:
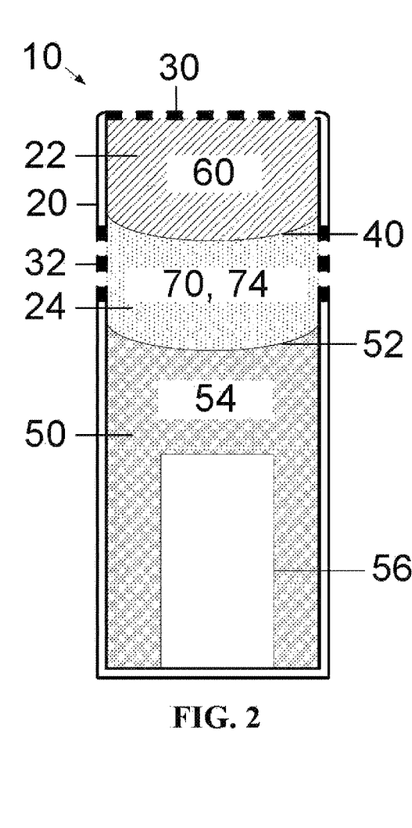
FIG. 2 shows a schematic sectional illustration of a first variant of a biosensor according to at least one embodiment of the invention.

FIG. 2 shows a further embodiment of a biosensor according to one or more embodiments of the invention. In at least one embodiment, the sensor material 60 may be or may include a hydrogel as discussed above regarding FIG. 1. In one or more embodiments, both an LCST hydrogel and a UCST hydrogel may be used.

As shown in FIG. 2, in one or more embodiments of the invention, the pressure sensor 56 may be arranged in a separate compartment 50, which borders the compartment 24 and may be separated therefrom by a membrane 52. In at least one embodiment, the pressure sensor 56 may be embedded in oil as transfer medium 54.

In one or more embodiments, the sensor material 60 may be arranged in a first compartment 22, and the compensation material 70 may be arranged in a second compartment 24. As shown in FIG. 2, by way of at least one embodiment, the compensation material 70 is not oil, but may include or may be a hydrogel 74, which includes a relationship between volume and temperature opposite that of the sensor material 60.

In at least one embodiment, the first compartment 22 that includes the sensor material 60 may be in contact with a test medium using a mechanical abutment 30, which is permeable to the medium and the analyte and may be embodied in the form of, or may include, a porous membrane. In one or more embodiments, the compensation material 70 may be in contact with a test medium via a mechanical abutment 32, which is arranged at least in regions at the side walls of the second compartment 24, is permeable to the medium and the analyte, and may be embodied in the form of, or may include, a porous membrane. In at least one embodiment, both compartments 22, 24 may be separated by a flexible membrane 40, which is flexible to enable the volume compensation between the compartment 22 and the compartment 24.

In one or more embodiments, a compensation of the temperature effect may be implemented by coordinating the hydrogel, such as sensor material 60, and the hydrogel 74, such as compensation material 70.

According to one or more embodiments, hydrogels as sensor material 60 having different cross-sensitivities, for example pH value, may be offset via the hydrogel 74 as compensation material. In at least one embodiment, the test medium rises over both hydrogels 60 and 74.

In one or more embodiments, the compensation material 70 may change its volume depending on the cross-sensitivity of the hydrogel as sensor material 60 with constant absolute value and reversed algebraic sign. In at least one embodiment, the swelling pressure in the pressure measurement chamber 20 may only be dependent on the measurement effect. In order to be able to adapt the hydrogels 60, 74 to one another in terms of their temperature dependencies, by way of one or more embodiments, pH value dependencies and/or dependencies of other cross-effects, the hydrogels 60, 74 may be modified during the synthesis within broad ranges, for example via cross-linking degree, used polymer proportion, and the like.

At least one embodiment of the invention may include a conventional membrane 52 between the compartment 24 and compartment 50, in which case the demands on membrane flexibility are not as high, since there is no membrane deflection by cross-sensitivity in the event of complete volume compensation between sensor material 60 and compensation material 70.

Figure 3:
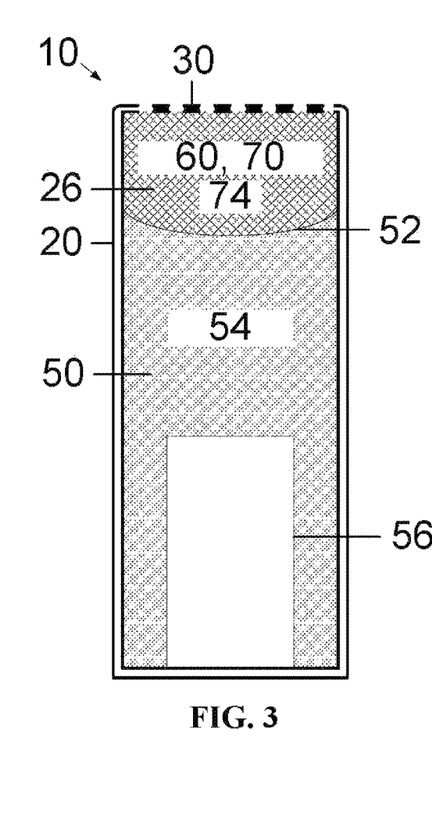
FIG. 3 shows a schematic sectional illustration of a first variant of a biosensor according to at least one embodiment of the invention.

FIG. 3 shows a further embodiment of a biosensor 10 according to one or more embodiments of the invention. In at least one embodiment, the sensor material 60 may be or may include a hydrogel and may be, as described above regarding FIG. 2, an LCST hydrogel or a UCST hydrogel. In one or more embodiments, the compensation material 70 may include or may be a hydrogel 74.

In at least one embodiment, the sensor material 60 may be mixed in the pressure measurement chamber 20 in a compartment 26 with the compensation material 70 and may form a stack arrangement that includes alternating layers of sensor material 60 and compensation material 70 or may be a mixture of particles of sensor material 60 and compensation material 70. In one or more embodiments, due to the mechanical abutment 30, which is permeable to the medium and the analyte and which may be embodied in the form of, or may include a porous membrane, the sensor material 60 and compensation material 70 may come into contact in the compartment 26 with a test medium.

In at least one embodiment, the pressure sensor 56 may be arranged in a manner bordering on the compartment 26 in a compartment 50, which may be filled with a pressure transfer medium 54, for example oil. In one or more embodiments, a membrane 52 may be arranged between the compartment 26 and compartment 50.

In at least one embodiment, a compensation of the temperature effect in the sensor material 60 and compensation material 70 may be implemented by mixing the hydrogel of the sensor material 60 and the hydrogel of the compensation material 70.

One or more embodiments of the invention may not include a membrane between the sensor material 60 and compensation material 70. In at least one embodiment, a conventional membrane 52 may be provided between the compartment 26 and compartment 50, in which case the demands on membrane flexibility are not as high, since there is no membrane deflection by cross-sensitivity in the event of complete volume compensation between sensor material 60 and compensation material 70.

Figure 4:
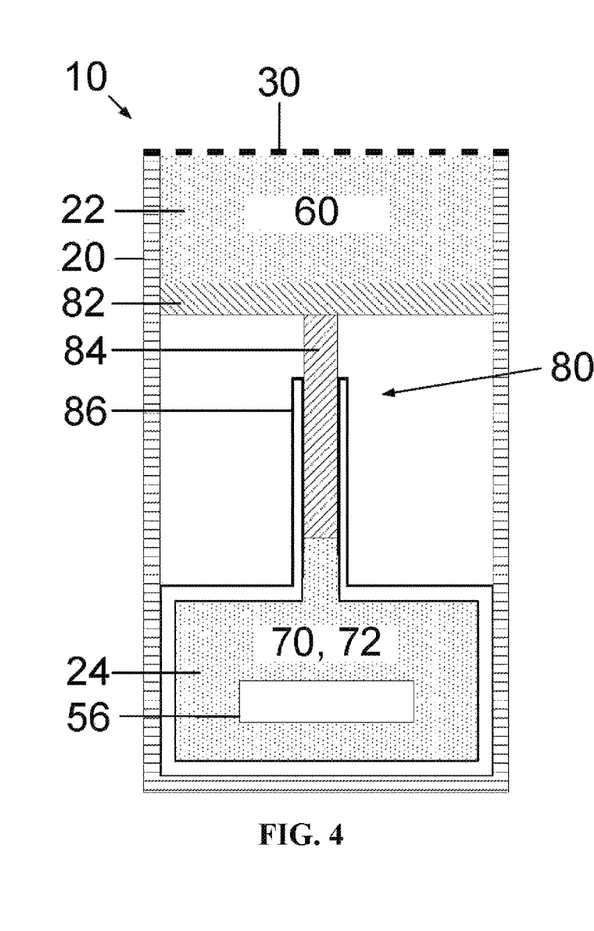
FIG. 4 shows a schematic sectional illustration of a first variant of a biosensor according to at least one embodiment of the invention.
Figure 5:
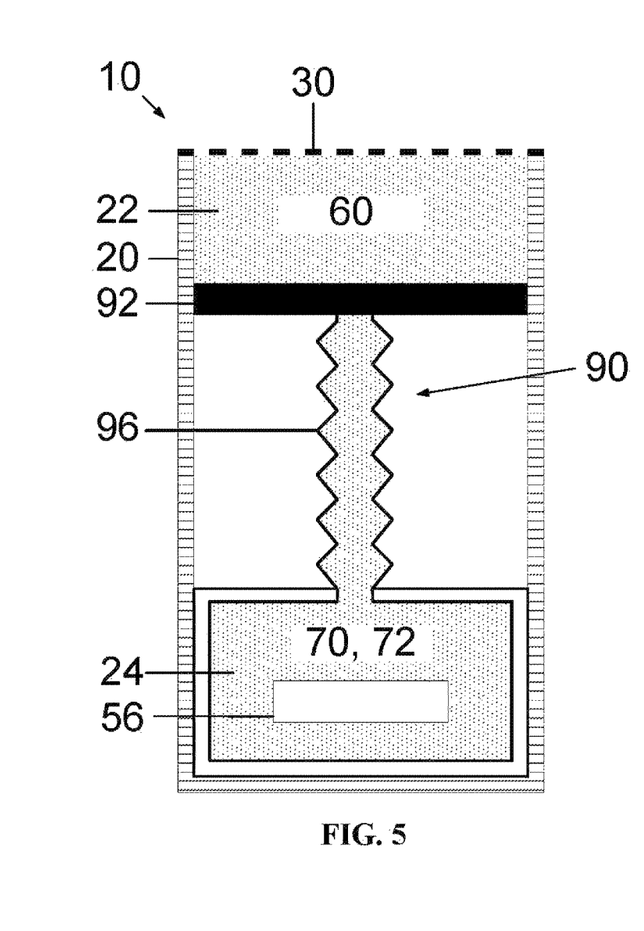
FIG. 5 shows a schematic sectional illustration of a first variant of a biosensor according to at least one embodiment of the invention.

FIGS. 4 and 5 show two further exemplary embodiments of biosensors 10 according to one or more embodiments of the invention. As shown in FIGS. 4 and 5, in at least one embodiment of the invention, the compensation material 70, similarly to the embodiments discussed above regarding FIG. 1, may be or may include an oil 72, which includes a relationship between volume and temperature opposite that of the sensor material 60. In one or more embodiments, the sensor material 60 may be arranged in a first compartment 22, and the compensation material 70 may be arranged in a second compartment 24 of the pressure measurement chamber 20. In at least one embodiment, the test medium may be in contact with the hydrogel, such as sensor material 60, via a mechanical abutment 30, which is permeable to the medium and the analyte and which may be embodied in the form of, or may include, a porous membrane.

One or more embodiments may include a pressure sensor 56, for example an ASIC module, in the oil 72 in the second compartment 24. In at least one embodiment, the pressure of the surrounding oil 72 may be measured.

As shown in FIGS. 4 and 5, in at least one embodiment of the invention, the variants may allow for a reduction/increase of the oil volume necessary per dry mass of the hydrogel, such as sensor material 60, via a hydraulic approach.

As shown in FIG. 4, according to one or more embodiments, the change in volume of the sensor material 60 in the compartment 22 may be forwarded via a pressure piston connection 80 to the oil 72 in the compartment 24 and the pressure sensor 56 embedded therein.

In at least one embodiment, the amplification of the oil expansion to compensate for the oil volume in the second compartment 24 may be achieved via the pressure piston connection 80. In one or more embodiments, in the event of a volume increase of the oil 72, a piston 84 guided in a guide 86 may be pressed upwardly. In at least one embodiment, the volume of the pressure measurement compartment 22, in which the hydrogel is located as sensor material 60, may then be corrected by the lifting table 82 depending on temperature.

As shown in FIG. 5, according to one or more embodiments of the invention, the change in volume of the sensor material 60 in the compartment 22 may be forwarded via an extendable pipe connection 90 to the oil 72 in the compartment 24 and the pressure sensor 56 embedded therein.

In at least one embodiment, the intensification of the compensation by the oil expansion in the second compartment 24 may be achieved via the extendable pipe connection 90. In one or more embodiments, in the event of an increase in volume of the oil 72, the lifting table 92 may be pressed upwardly. In at least one embodiment, the volume of the compartment 22, in which the hydrogel is located as sensor material 60, may then be corrected depending on temperature by the lifting table 92.

One or more embodiments may estimate the oil volume/hydrogel dry mass ratio with 1:n conversion, wherein a 1:n conversion may be defined herein as the change in volume of the oil 72 leads to an n-times compensation volume at the hydrogel, such as sensor material 60, via an amplification principle.

In at least one embodiment, an amplification may be implemented by reducing the cross section of the mechanism, such as the piston cross section $A_{84}$ in FIG. 4 or the pipe cross section $A_{96}$ in FIG. 5 compared with the area of the lifting table 82 ($A_{82}$), 92 ($A_{92}$) in accordance with the hydrogel area. In one or more embodiments, the cross-sectional areas $A_{84}$ and $A_{96}$ are referred to herein as $_{AM}$, and the cross-sectional areas $A_{82}$ and $A_{92}$ are referred to herein as $_{AH}$.

In at least one embodiment, compensation may be defined as the amplified temperature-induced change in the oil volume $\Delta V_{72}$ corresponds to the temperature-induced change in the hydrogel volume $\Delta V_{60}$ accompanied by water absorption/release, with $n*\Delta V_{72}/\Delta T = -\Delta V_{60}/\Delta T$.

In at least one embodiment, including lifting table 82, 92, a ratio of the volume $V_{72}$ of the oil 72 to the dry mass $m_{60}$ of the hydrogel, such as sensor material 60, of $V_{72}/m_{60}$ equals 360 µl/mg may be given for a present hydrogel, such as sensor material 60. Without conversion, in one or more embodiments, an oil volume of $V_{72}=720$ µl may be necessary for complete compensation in the case of a filling with $m_{60}=2$ mg. In at least one embodiment, a possible conversion may result from $_{AM}=10*_{AH}$. With the described conversion n=10, in one or more embodiments, the oil volume $V_{72}$ may reduce to 72 µl for complete compensation in the event of a filling with $m_{60}=2$ mg. In at least one embodiment, an adaptation of the hydrogel quantity may be possible with a 1:n conversion. If complete compensation or an overcompensation of the temperature dependency is not desired, in one or more embodiments, the ratio $V_{72}/m_{60}$ of the oil volume $V_{72}$ to the dry mass $m_{60}$ may be adapted accordingly.

According to one or more embodiments, as described in FIGS. 1-5, the biosensor 10 may be used to detect or concentrate measurement of components in the blood as test medium. In at least one embodiment, since the measurement effect is dependent on the material of the used hydrogel, such as sensor material 60, the design may be of a platform nature. By way of one or more embodiments, a glucose sensor may be used for a glucose-sensitive hydrogel as sensor material 60.

Figure 6:
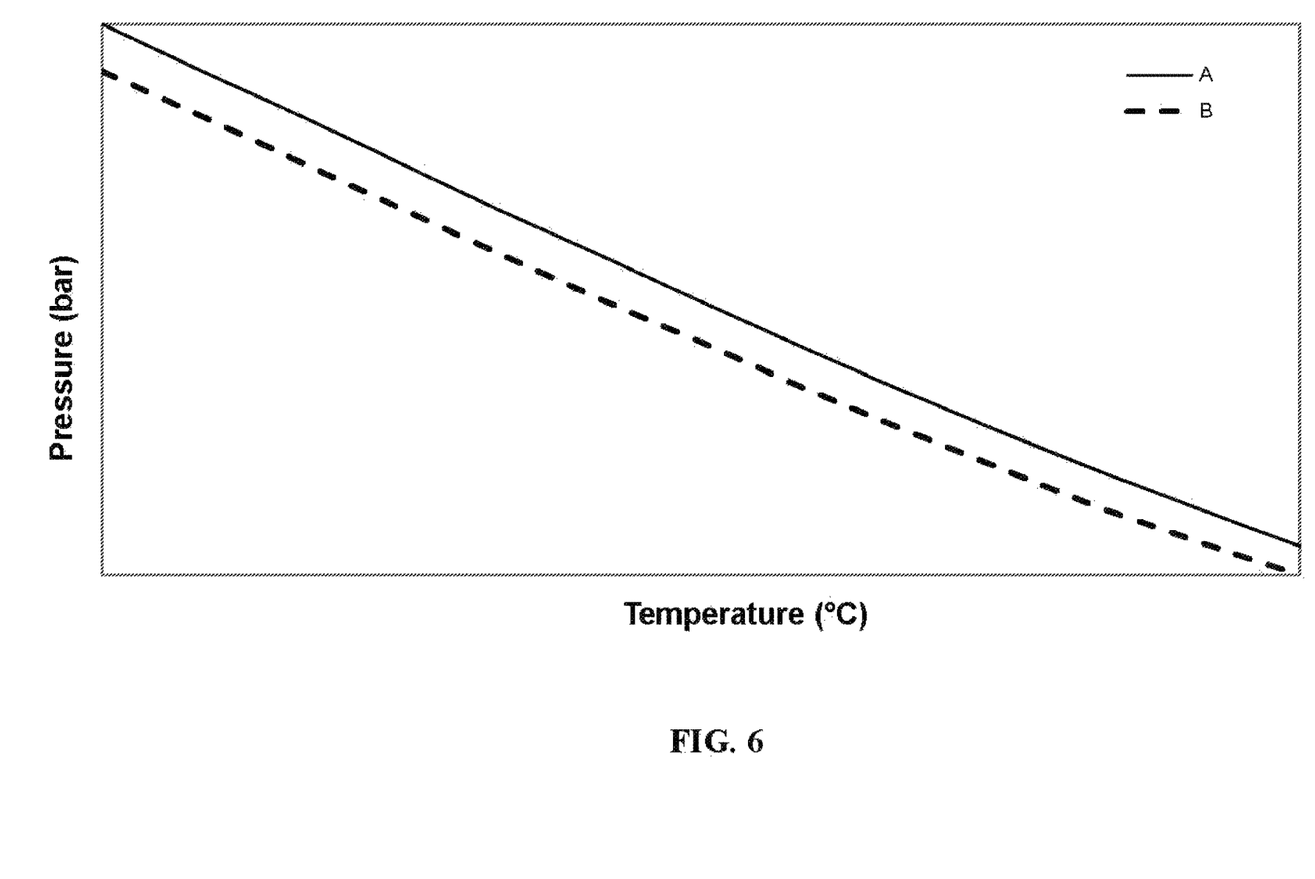
FIG. 6 shows a schematic illustration of a graph with reversible shift of the pressure change by binding potassium using a potassium-sensitive hydrogel.

FIG. 6 shows measurement curves A, B of a potassium-sensitive hydrogel for a temperature range typical for an implant, according to one or more embodiments of the invention. As shown in FIG. 6, in at least one embodiment, curve A shows the course of the pressure p over temperature T without potassium in the test medium. In one or more embodiments, curve B shows the course with potassium addition.

In isochoric conditions, for example conditions with constant volume of the sensor material 60, in one or more embodiments, the hydrogel may present a potassium-dependent shift of the pressure-temperature curve. In at least one embodiment, the addition of $KNO_3$ may shift the curve to the left from A to B in FIG. 6.

In one or more embodiments, the temperature dependency of the volume and therefore the pressure may decisively influence the sensitivity. In at least one embodiment, the dependency may be dependent on the hydrogel formulation. By way of one or more embodiments, as a result of a lesser use of the used cross-linker(s), a greater temperature-dependent volume change and therefore pressure change may be observed based on the resultant reduced restoring forces. In at least one embodiment, the filling degree of the hydrogels, such as sensor material 60 and compensation material 70, in the pressure measurement chamber 20 of the potassium-sensitive biosensor 10 may influence the temperature-dependent pressure change. In one or more embodiments, the filling degree may include the used dry mass of hydrogel per volume. In at least one embodiment, if more dry mass of the hydrogel, such as sensor material 60 and compensation material 70, is introduced into the predefined volume of the pressure measurement chamber 20, the rise in the pressure-temperature curves may be increased, which results in a higher sensitivity of the biosensor 10 at the measurement temperature and with a given relationship between volume (pressure) and temperature.

One or more embodiments of the invention, with hydrogels that contain identifying components for potassium, may detect changing potassium concentrations via changes in pressure. In at least one embodiment, with the biosensor 10, the difficult problem of separating temperature changes from changes in the potassium concentration may be solved. Technical considerations have shown that the determination of temperature that would be necessary for a measurement without temperature compensation may be achieved from a technical viewpoint at the required level only with difficulty, in particular in the implant model. In the case of the potassium-sensitive hydrogel, presented by way of example, the requirement of a resolution of 0.1 mM potassium concentration is accompanied by the requirement of a temperature resolution, necessary for assessment of the temperature and potassium influence at the measurement pressure, of less than 7.5 mK without use of the sensor according to embodiments of the invention. In the event of complete compensation by the sensor, according to one or more embodiments of the invention, the temperature measurement may be omitted in full. If the compensation succeeds with use of the sensor, according to one or more embodiments the invention, with a tolerance of 5%, the necessary temperature measurement resolution may increase by a factor of 20 to 150 mK. In at least one embodiment, such as value may easily be achieved by integrated temperature sensors based on microsystem technology. At the same time, in one or more embodiments, the sensitivity to the analyte to be detected (determined by potassium-dependent pressure change) may remain uninfluenced thereby.

In one or more embodiments, the compensation material 70, in order to fully eliminate the temperature-dependent change in pressure of the sensor material 60 in the form of an LCST hydrogel, may include a positive relationship between volume and temperature, wherein the temperature-dependent change in volume of the compensation material compensates for the temperature-dependent change in volume of the sensor material. When heated, according to at least one embodiment of the invention, the hydrogel may be provided with a smaller volume, and when cooled, may be provided with a greater volume. In one or more embodiments, such a process may occur in an isobaric manner, i.e. with no pressure change.

In at least one embodiment of the invention, the potassium sensitivity may remain uninfluenced because the hydrogel, such as sensor material 60, still absorbs/releases water depending on the potassium concentration. In one or more embodiments, such a change may occur in an isochoric manner, i.e. at constant volume. In at least one embodiment, by decoupling the two effects, temperature dependency and potassium sensitivity, via division into isobaric (→compensation of the temperature dependency) and isochoric (→potassium sensitivity) state changes, the potassium concentration may be determined with a high level of precision in the presence of fluctuating temperatures. By way of one or more embodiments, the combination of sensor material 60 and compensation material 70 with opposed temperature dependencies with respect to pressure and volume may enable a combination of isochoric and isobaric state changes. In at least one embodiment, a highly accurate temperature measurement that is difficult to perform from a technical viewpoint, in particular in the typical implant model, may no longer be necessary in such cases.

According to one or more embodiments, the compensation material 70 may be formed such that other cross-sensitivities, for example pH value, of the used hydrogel or all usable polymers and test media may be compensated for.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A biosensor (10) comprising:
a sensor material (60);
a pressure measurement chamber (20);
a pressure sensor (56); and
a compensation material (70);
wherein said sensor material (60) is sensitive to at least one analyte;
wherein said sensor material (60) is in the pressure measurement chamber (20),
wherein said compensation material (70) is in the pressure measurement chamber (20),
wherein said pressure measurement chamber (2) is (20) is coupled to the pressure sensor (56),
wherein a pressure prevailing in the pressure measurement chamber (20) is determined by the pressure sensor (56),
wherein the sensor material (60) is configured to undergo a change in volume in response to a cross-sensitivity of the sensor material (60) comprising a change to at least one ambient variable detected at said sensor material (60),
wherein the compensation material (70) is configured to undergo a change in volume in response to a change to the at least one ambient variable, and wherein the change in volume of thr compensation material (70) is opposite to the change in volume of the sensor material (60),
such that the change in volume of the sensor material (60) is at least partially compensated for by the change in volume of the compensation material (70).

2. The biosensor according to claim 1, wherein the cross-sensitivity-induced change in volume of the sensor material (60) is one or more of a temperature-induced change in volume and a pH value-induced change in volume.

3. The biosensor according to claim 1, wherein the sensor material (60) sensitive to at least one analyte is a polymer gel, or hydrogel, or a smart hydrogel sensitive to at least one analyte.

4. The biosensor according to claim 1, wherein said at least one ambient variable detected at said sensor material (60) comprises one or more of a change to a pH value, temperature change, and change in concentration of the at least one analyte.

5. The biosensor according to claim 1, wherein the pressure measurement chamber (20) comprises at least two compartments (22, 24), wherein the sensor material (60) is arranged in a first compartment of the at least two compartments and the compensation material (70) is arranged in a second compartment of the at least two compartments, and wherein the first compartment comprises a region (30) which is permeable to the at least one analyte and a test medium.

6. The biosensor according to claim 5, wherein
the first compartment and the second compartment border one another, or
the biosensor further comprises a flexible membrane (40) arranged between the first compartment and the second compartment, or
both wherein the first compartment and the second compartment border one another and wherein the biosensor further comprises a flexible membrane (40) arranged between the first compartment and the second compartment.

7. The biosensor according to claim 6, wherein said second compartment comprises a region which is permeable to the at least one analyte and the test medium.

8. The biosensor according to claim 5, wherein the pressure sensor (56) is arranged at least in part in the second compartment and wherein regions of the pressure sensor (56) are surrounded by the compensation material (70).

9. The biosensor according to claim 8, wherein the compensation material (70) is oil (72).

10. The biosensor according to claim 1, wherein the pressure measurement chamber (20) comprises one compartment (26), wherein the sensor material (60) is mixed in the pressure measurement chamber (20) with the compensation material (70) within the one compartment (26), and wherein the one compartment (26) comprises a mechanical abutment which is permeable to the at least one analyte and a test medium.

11. The biosensor according to claim 10, wherein the sensor material (60) together with the compensation material (70) form a stack arrangement comprising alternating layers of sensor material (60) and compensation material (70), or wherein the sensor material (60) together with the compensation material (70) comprise a mixture of particles of sensor material (60) and compensation material (70).

12. The biosensor according to claim 1, wherein the pressure sensor (56) is arranged within the pressure measurement chamber (20) in an additional compartment (50), wherein the additional compartment (50) is filled with a pressure transfer medium (54).

13. The biosensor according to claim 5, wherein the first compartment (22) is coupled to the second compartment (24) by a pressure piston connection (80) or by an extendable pipe connection (90), such that a change in volume of the first compartment (22) leads to a change in volume of the second compartment (24).

14. The biosensor according to claim 1, wherein the compensation material (70) is a hydrogel.

15. The biosensor according to claim 1, wherein the biosensor (10) is configured to be implanted in a human or animal body.

16. The biosensor according to claim 1, wherein the pressure measurement chamber (20) comprises a wall, and wherein
the pressure sensor (56) is connected to the wall of the pressure measurement chamber (20), or
one or more components of the pressure sensor (56) are part of the wall of the pressure measurement chamber (20).

* * * * *